United States Patent [19]

Spector

[11] Patent Number: 4,665,901

[45] Date of Patent: May 19, 1987

[54] PERIODONTAL FINGER APPLICATOR

[76] Inventor: Donald Spector, 380 Mountain Rd., Union City, N.J. 07087

[21] Appl. No.: 844,623

[22] Filed: Mar. 27, 1986

[51] Int. Cl.4 .............................................. A61H 7/00
[52] U.S. Cl. ..................................... 128/62 A; 401/7; 401/8; 604/82; 604/87
[58] Field of Search ...................... 128/62 A; 401/7, 8; 604/3, 82, 87, 88, 244, 289, 292, 306

[56] References Cited

U.S. PATENT DOCUMENTS

| | | | |
|---|---|---|---|
| 1,255,925 | 2/1918 | Peters | 401/8 |
| 1,896,941 | 2/1933 | Cohen | 401/7 |
| 2,016,951 | 10/1935 | Welker | 401/7 |
| 2,061,219 | 11/1936 | Wright | 401/7 |
| 2,077,540 | 4/1937 | Welker | 128/62 A |
| 2,121,701 | 6/1938 | Landers | 128/62 A |
| 2,445,477 | 7/1948 | Folkman | 604/87 |
| 3,589,819 | 6/1971 | Bryant | 401/7 |
| 3,636,922 | 1/1972 | Ketner | 604/289 |
| 3,757,782 | 9/1973 | Aiken | 604/3 |
| 3,981,304 | 9/1976 | Szpur | 604/3 |
| 4,608,043 | 8/1986 | Larkin | 604/87 |

Primary Examiner—John J. Wilson
Assistant Examiner—Adriene J. Lepiane
Attorney, Agent, or Firm—Michael Ebert

[57] ABSTRACT

A disposable finger applicator adapted to facilitate the application of a two-component therapeutic agent to gum tissues for treating periodontal disease. The applicator includes a collapsible thimble which when in use fits on the index finger of the user, the thimble being bonded to the rear wall of a small envelope formed of opaque, non-stretchable film material containing a charge of hydrogen peroxide in an aqueous solution. Marginally secured to the front wall of the envelope and otherwise spaced therefrom to define an internal cavity is an outer layer of porous, sponge-like material, the cavity being filled with dry sodium bicarbonate powder. The front wall of the envelope is provided with a weakened zone, such that when the finger applicator is pressed by the user against gum tissue, the hydrogen peroxide solution trapped in the envelope then ruptures the weakened zone, thereby causing the solution to leak into the cavity and to intermingle with the sodium bicarbonate powder. The resultant slurry impregnates the outer layer and is extruded therefrom as the applicator is rubbed along the gums to therapeutically treat the tissues thereof and to at the same time stimulate the tissues.

6 Claims, 3 Drawing Figures

U.S. Patent May 19, 1987 4,665,901
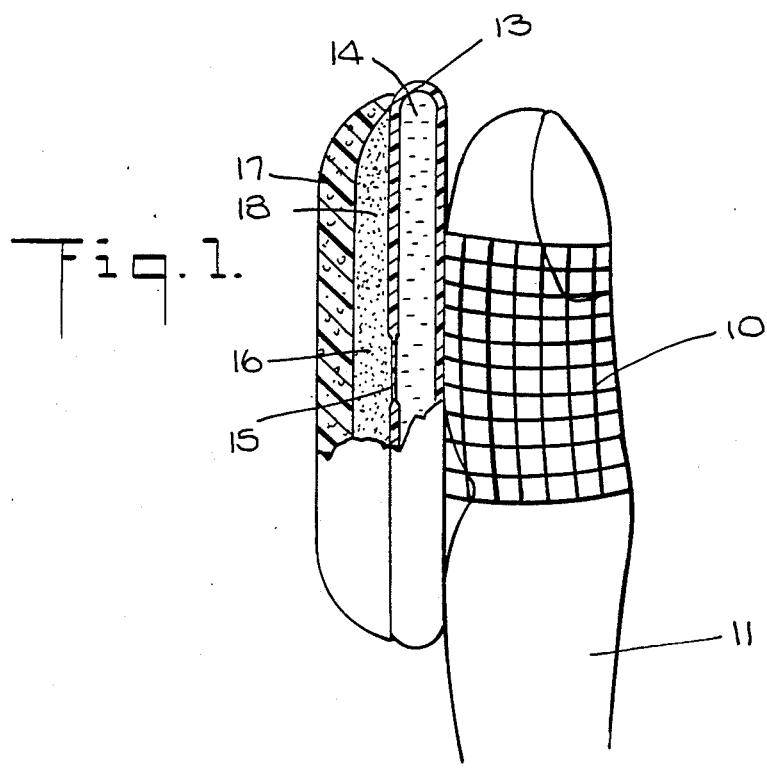
Fig.1.
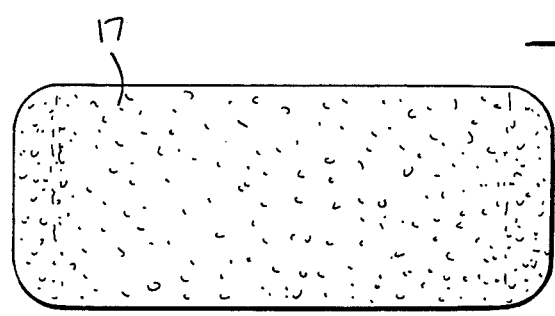
Fig.2.
Fig.3.
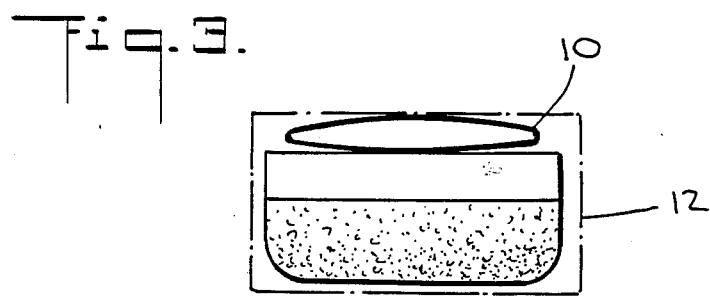

PERIODONTAL FINGER APPLICATOR

BACKGROUND OF INVENTION

1. Field of Invention

This invention relates generally to the treatment of periodontal disease, and in particular to a finger applicator which facilitates the application of a therapeutic agent to gum tissue.

2. Status of Prior Art:

Periodontal disease which results in inflammation or degeneration of the tissues which surround and support the teeth most commonly begins with gingivitis and progresses to periodontis. The greatest single causative factor in gingivitis which involves the inflammation of the gum tissue and is characterized by swelling and bleeding, is bacterial plaque. Such plaque is formed by microbial colonies growing on the tooth surface.

The usual treatment for periodontal disease is plaque control by good oral hygiene. But however diligent one is in practicing oral hygiene by removing plaque with dental floss and a toothbrush, in many cases microbial colonies somehow manage to establish themselves on the tooth surfaces. It then becomes necessary to use chemical treatment to destroy microbial activity.

Highly effective for this purpose is the combined use of hydrogen peroxide ($H_2O_2$) and baking soda (sodium bicarbonate). Hydrogen peroxide, which is usually available in aqueous solutions of various strengths, acts as a strong oxidizing agent and therefore destroys the anaerobic bacteria present in plaque. Baking soda, which is often used as a mouthwash, acts synergistically in combination with hydrogen peroxide as a therapeutic agent for periodontal disease.

Because of certain practical problems, individual are often discouraged from making daily use of hydrogen peroxide and baking soda for gum treatment. Hydrogen peroxide is fundamentally unstable and must be separately stored in a lightexcluding bottle. Sodium bicarbonate is soluble in water and is stable only in dry air; for in moist air it slowly decomposes. Hence, sodium bicarbonate must be stored in a tightly sealed container.

If, therefore, one is required to treat the gums with hydrogen peroxide in combination with baking soda, these ingredients must be properly stored in separate containers. Each time a treatment is called for, one must then open these containers and remove small amounts from each and intermix the ingredients to create the desired therapeutic agent, being careful to then close the containers.

And in order to apply this therapeutic agent to the gums, a toothbrush is generally used as the applicator. While a toothbrush works well with a dentifrice in paste form which sticks to the bristles, the toothbrush is less effective with a slurry formed by baking soda and hydrogen peroxide. Moreover, toothbrushes are not always in a sterile condition.

Since the present invention provides a periodontal finger applicator having separate compartments therein containing hydrogen peroxide and baking soda, the prior art relating to finger-type dental applicators is of background interest.

The 1976 patent to McCord, U.S. Pat. No. 3,952,867, shows a disposable tooth cleaner in the form of a sealed package having two separate compartments, one having toothpaste therein and the other storing a finger applicator whose outer layer is formed by a fabric capable of supporting the toothpaste. The 1962 MacDonald U.S. Pat. No. 3,070,102 discloses a throwaway toothbrush adapted to adhere to a finger of the user, toothpaste being embedded in the bristles.

In the 1935 Welker U.S. Pat. No. 2,016,951, the dental cleaner is of the cot type which fits on a finger and has a rubbing strip thereon for cleaning the teeth and stimulating the gums. In this device, a charge of toothpaste is contained in a sealed plastic envelope which is ruptured only when the finger is bent to release the toothpaste. In the 1937 Welker U.S. Pat. No. 2,077,540, a finger cot dental cleaner is provided in which the toothpaste is in a reservoir covered by a thin film which is ruptured to release the toothpaste when pressure is applied to the reservoir. A similar scheme is shown in the 1937 Welker U.S. Pat. No. 2,075,681.

Other forms of finger type dental applicators are shown in the following patents:

| | |
|---|---|
| Over | 1,144,777 |
| Homburger | 3,176,338 |
| Hobelman | 2,419,896 |
| Cohen | 1,896,941 |
| Vaughan | 2,915,767 |
| Holton | 2,921,590 |

None of the finger applicators disclosed in the above prior art patents is adapted to provide a therapeutic agent to the gum tissues of the user.

SUMMARY OF INVENTION

In view of the foregoing, the main object of this invention is to provide a finger applicator to facilitate the application of a two-component therapeutic agent to gum tissues for treating periodontal disease.

More particularly, an object of this invention is to provide a disposable applicator which applies to the gums a slurry of sodium bicarbonate powder and a solution of hydrogen peroxide.

A significant advantage of an applicator in accordance with the invention is that when the applicator is not in use, a charge of hydrogen peroxide solution container therein is maintained in a stable condition and a charge of sodium bicarbonate powder is separately maintained in a stable dry state, these ingredients not being intermingled until the applicator is put to use.

Also an object of the invention is to provide an applicator which, as gum tissues are being treated, also functions to stimulate the tissues.

Still another object of the invention is to provide an inexpensive, disposable applicator which makes it possible for a user without difficulty and at low cost to carry out daily treatment of his gums.

Briefly stated, these objects are attained in a disposable finger applicator adapted to facilitate the application of a two-component therapeutic agent to gum tissues for treating periodontal disease. The applicator includes a collapsible thimble which when in use fits on the index finger of the user, the thimble being bonded to the rear wall of a small envelope formed of opaque, non-stretchable film material containing a charge of hydrogen peroxide in an aqueous solution. Marginally secured to the front wall of the envelope and otherwise spaced therefrom to define an internal cavity is an outer layer of porous, sponge-like material, the cavity being filled with dry sodium bicarbonate powder. The front wall of the envelope is provided with a weakened zone, such that when the finger applicator is pressed by the user against gum tissue, the hydrogen peroxide solution trapped in the envelope then ruptures the weakened zone, thereby causing the solution to leak into the cavity and to intermingle with the sodium bicarbonate powder. The resultant slurry impregnates the outer layer and is extruded therefrom as the applicator is rubbed along the gums to therapeutically treat the tissues thereof and to at the same time stimulate the tissues.

OUTLINE OF DRAWINGS

For a better understanding of the invention as well as other objects and further features thereof, reference is made to the following detailed description to be read in conjunction with the accompanying drawings, wherein:

FIG. 1 illustrates a periodontal applicator in accordance with the invention on the index finger of the user, the structure of the operating elements of the applicator being shown in section;

FIG. 2 is a plan view of the applicator; and

FIG. 3 is an end view of the applicator when housed in a sealed package.

DESCRIPTION OF INVENTION

Referring now to the figures of the drawing, a periodontal finger applicator in accordance with the invention includes a collapsible thimble 10 which fits on the index finger 11 of a user. Thimble 10 may be formed of a somewhat stretchable synthetic film material or of an elastomeric woven or non-woven fabric, so that the thimble will accommodate itself to index fingers of different thicknesses. This thimble, as shown in FIG. 3, when the applicator is stored in a sealed package represented by the dashed-line rectangle 12, is then flattened to make possible a more compact package.

Thimble 10 is bonded or otherwise attached to the rear wall of a generally rectangular small envelope 13 formed of synthetic plastic film material which is non-stretchable and opaque so as to exclude light. Suitable for this purpose is bi-axially oriented Mylar (polyester) film. Envelope 13 is completely filled with a charge 14 of a hydrogen peroxide aqueous solution in a concentration appropriate to periodontal gum treatment.

The front wall of envelope 13 is provided with a weakened zone 15. In the case of Mylar, this zone can be created by impressing a heated die on the surface of the Mylar to form score lines thereon. Because Mylar loses its bi-axial molecular orientation when subjected to heat at a temperature close to its fusion point, the Mylar material along the lines is quite weak and easily ruptured. In other cases, the film may be provided with deep score lines to weaken its structure.

Marginally secured to the front wall of envelope 13 but otherwise spaced therefrom to define an internal cavity 16 is a rectangular layer 17 formed of a sponge-like absorbent material such as flexible, open-cell polyurethane or polyvinyl foam. In practice, the margins of the layer may be thermally bonded by a heated die to the margins of the front wall of the envelope.

Cavity 16 is filled with a charge 18 of dry sodium bicarbonate powder. Because layer 17 is relatively thick, it normally acts as a barrier to exclude moist air from the powder. In any event, when the applicator is stored in a package 12, it is hermetically sealed therein to exclude moist air. The package may be in the form of a heat-sealed film envelope. The outer face of layer 17 is preferably relatively coarse so that when the applicator is rubbed along the surface of gum tissues by the user, it acts to stimulate the tissues.

In operation, when the applicator is on the index finger of the user, and is then pressed against the tissues of the gums, envelope 13 within which the hydrogen peroxide solution is trapped is then subjected to compression. But since the solution is non-compressible, it acts to rupture the weakened zone 15, as a result of which the solution leaks into cavity 16 and intermingles with the dry powder 18 therein to form a slurry. This slurry impregnates the absorbent layer 17 to form a two-component therapeutic agent that is extruded from the layer as the applicator is rubbed along the gum tissues.

The dosage of ingredients in the finger applicator is sufficient for a single daily treatment. The applicator is initially sterile and is stored in a sterile package. Since the applicator is discarded after a single use, there is no problem of sterility, as with a toothbrush. In practice, a user will stock a substantial supply of packaged applicators so as to have them available at all times. The same applicator, because of the baking soda, functions as a dentifrice; hence, it may also be used as an emergency toothbrush.

While there has been shown and described a preferred embodiment of a periodontal finger applicator in accordance with the invention, it will be appreciated that many changes and modifications may be made therein without, however, departing from the essential spirit thereof.

Thus, instead of an applicator having a thimble which fits on the finger of a user, the applicator can be provided with a handle. And while the invention has been disclosed for periodontal treatment, the same applicator structure can be used for cosmetic purposes in which the ingredients are normally separated cosmetic ingredients. For example, in the envelope, one may store a liquid collagen or a colloidal dispersion thereof, and in the cavity one may store a facial cream which when the envelope is ruptured is intermingled with the liquid to produce a slurry that is extruded by the sponge layer.

I claim:

1. A disposable finger applicator adapted to facilitate the application of a two-component therapeutic agent to gum tissues for treating a periodontal condition, said applicator comprising:

A a thimble which fits onto the index finger of the user;

B a small envelope formed of opaque flexible film material containing a sealed charge of hydrogen peroxide in an aqueous solution, the opaque film excluding light from the solution, the rear wall of the envelope being bonded to one side of the thimble, the front wall of the envelope having a weakened zone therein; and C a layer of absorbent sponge-like material marginally secured to the front wall of the envelope and otherwise spaced therefrom to define therewith an internal cavity, said cavity being filled with dry sodium bicarbonate powder with respect to which the layer is impervious and normally acts as a barrier to maintain the dry powder within the cavity, whereby when the applicator is pressed against gum tissue by the user, the resultant pressure effects rupture of the weakened zone, thereby causing the solution in the envelope to leak into the cavity and intermingle with the powder to form a slurry that impregnates the layer which no longer acts as a barrier and is extruded therefrom as the layer is rubbed along the gum tissues.

2. An applicator as set forth in claim 1, wherein said thimble is formed of flexible material and is collapsible.

3. An applicator as set forth in claim 2, wherein said thimble is formed of an elastomeric fabric to conform to different sizes of index fingers.

4. An applicator as set forth in claim 1, wherein said envelope is formed of bi-axially oriented, high strength polyester film.

5. An applicator as set forth in claim 4, wherein said weakened zone is formed by a non-oriented polyester region.

6. An applicator as set forth in claim 1, wherein said layer is formed of open-cell, flexible foam plastic material.

* * * * *